United States Patent [19]

Kaplan et al.

[11] Patent Number: 4,909,710
[45] Date of Patent: Mar. 20, 1990

[54] LINEAR PERISTALTIC PUMP

[75] Inventors: David E. Kaplan, Moraga, Calif.;
David Burkett, Jonesboro, Ga.;
Laurence Warden, San Diego, Calif.

[73] Assignee: Fisher Scientific Company,
Pittsburgh, Pa.

[21] Appl. No.: 425,473

[22] Filed: Oct. 23, 1989

[51] Int. Cl.⁴ ............................................. F04B 43/12
[52] U.S. Cl. ..................................... 417/53; 417/474;
604/153
[58] Field of Search ................. 417/53, 474, 475, 478,
417/479; 604/153

[56] References Cited

U.S. PATENT DOCUMENTS

| | | | |
|---|---|---|---|
| 3,606,596 | 9/1971 | Edwards | 417/474 X |
| 3,658,445 | 4/1972 | Pulman et al. | 417/474 |
| 4,482,347 | 11/1984 | Borsanyi | 417/474 X |
| 4,653,987 | 3/1987 | Tsuji et al. | 417/474 X |
| 4,725,205 | 2/1988 | Cannon et al. | 417/474 X |
| 4,728,265 | 3/1988 | Cannon | 417/474 X |
| 4,731,057 | 3/1988 | Tanaka et al. | 604/153 |
| 4,755,109 | 7/1988 | Botts | 417/474 X |
| 4,781,548 | 11/1988 | Alderson et al. | 417/474 |
| 4,836,752 | 6/1989 | Burkett | 417/474 X |

*Primary Examiner*—Leonard E. Smith
*Assistant Examiner*—Eugene L. Szczecina, Jr.
*Attorney, Agent, or Firm*—Nydegger & Harshman

[57] ABSTRACT

A linear peristaltic pump equipped with a pressure relief mechanism for pumping I.V. fluids to a patient comprises a platen for supporting the tube, and a plurality of fingers which sequentially urge against the tube resting against the platen for creating a moving zone of occlusion. Cam lobes are formed to lift a penultimate and ultimate finger off of the tube at a rate faster than the other fingers to prevent pressure increases inside the tube which would otherwise be caused by other fingers urging against the tube. Additionally, the ultimate finger may be shortened with respect to the other fingers to reduce the total occlusion time of the ultimate finger to provide a more linearized flow of fluid to the patient.

16 Claims, 3 Drawing Sheets

LINEAR PERISTALTIC PUMP

BACKGROUND OF THE INVENTION

The present invention relates generally to peristaltic pumps which are used to pump fluid through resilient tubes. More particularly, the present invention relates to the drive mechanism of a linear peristaltic pump which minimizes the pulsatile effects of peristaltic pumps. The present invention is particularly, but not exclusively, useful in the health care field for the intravenous administration of medical solutions to patients.

DISCUSSION OF THE PRIOR ART

Several pumps have been proposed which are specifically and uniquely designed for intravenous (I.V.) infusion of medical solutions to patients. The objective in each instance is to provide a pump which can reliably and accurately control the flow of fluid to the patient. Of the many types of pumps used for I.V. infusion, the present invention is concerned with that type which exerts a peristaltic action on the tube through which the fluid is being pumped. Specifically, the present invention is concerned with pumps which fall generally into the category of linear peristaltic pumps.

Although the actual design for a linear peristaltic pump will differ from pump to pump, linear peristaltic pumps generally require the mechanical interaction of the following basic elements: a platen; a resilient tube through which fluid is to be pumped which rests against the platen; a peristaltic mechanism (i.e. structure capable of creating a moving zone of occlusion along the tube); and a driven mechanism for the peristaltic mechanism. The peristaltic mechanism must operatively engage the I.V. tubing through which the medical solutions are to be pumped. As is well known by the skilled artisan, this engagement requires positioning of the tube between the platen and the peristaltic mechanism.

It should be apparent that for a moving zone of occlusion to be generated along the tube, the pump must squeeze the tube in some sequential manner. This squeezing action occurs as the result of relative movement between the peristaltic mechanism and the platen to correspondingly generate a force to squeeze fluid through the resilient tube. Problems arise in linear peristaltic pumps when the occlusion on the tube causes short term deformation of the tube, or allows excessive pressure to build up within the tube. This results in uncontrolled variations in fluid flow through the tube, and thus unwanted pulsatile flow, rather than the desired linear flow.

Some of the problems associated with a pulsatile flow of fluid can be alleviated by increasing the number of fingers making sequential contact with the tube. It has been found that the flow of fluid in a linear peristaltic pump becomes noticeably more linear in nature when the number of fingers exceeds eight (8). For practical purposes, it has been found that the number of fingers should range between eleven (11) and fourteen (14) to obtain the optimal linear pumping arrangement.

There are additional problems, however, associated with even an optimal number of fingers. Assuming for the moment that twelve (12) fingers are optimal for the operation of a linear peristaltic pump, during each cycle the first finger throug the twelfth finger will sequentially occlude the tube in a wave-like action to cause fluid flow through the tube. At the end of each cycle, the twelfth finger will be causing the tube to occlude. As the next cycle begins, there will be an interval in time during which the first finger will also be occluding the tube. During this interval of time, fluid is trapped between these two (2) points of occlusion (i.e. the first and twelfth finger) to create a pocket of fluid within the tube. While this pocket exists, the second, third and possibly subsequent fingers are also in the process of urging against the tube forming the pocket as they approach their respective points of occlusion on the tube. This causes the pressure to increase disproportionately in the pocket with respect to the downstream fluid pressure. Consequently, when the twelfth finger lifts off the tube to end the previous cycle, the balloon pressure created by the second and third fingers against the pocket causes fluid to surge from the pocket into the downstream tube. The result is a non-linear or pulsatile flow of fluid into the patient.

The present invention recognizes that the lift-off sequence of the peristaltic fingers (i.e. the sequence in which each finger starts or stops occluding the tube) can be varied in their relation to each other to provide a more uniform and less pulsatile fluid flow. Specifically, the present invention recognizes that the camming mechanism of a linear peristaltic pump can be set to establish a predictable response for the sequencing of individual finger occlusions which will tend to minimize surges in the resulting fluid flow through the tube.

In light of the above, the present invention recognizes the need for peristaltic pumps which are capable of continuously pumping fluid through a resilient tube while minimizing any pulsatile characteristics in the flow of fluid. Another object of the present invention is to provide a linear peristaltic pump which minimizes any fluid pressure changes in the fluid tube that can cause pulses or surges in fluid flow through the tube. Yet another object of the present invention is to provide a linear peristaltic pump which is easy to manufacture and relatively simple to operate. Yet another object of the present invention is to provide a durable and reliable peristaltic pump which is cost effective and which accurately infuses fluids to patients.

SUMMARY OF THE INVENTION

The preferred embodiment of the linear peristaltic pump having a pressure relief mechanism of the present invention comprises a plurality of fingers which press against an I.V. tube resting against a platen. Specifically, the plurality of fingers sequentially urge against the tube in wavelike fashion to create a moving of zone of occlusion along the tube for forcing fluids through the I.V. tube. The fingers are slidably housed inside a casing to guide the reciprocal movement of the fingers.

The fingers are operatively coupled to a camshaft which selectively controls the reciprocal displacement of each finger. Specifically, the camshaft has a plurality of cam lobes spaced in a helical relationship therealong to selectively move each respective finger between an open or up position and a closed or down position. Further, the camshaft is housed inside the casing and is connected to a motor for providing the necessary rotational movement.

In its operation, the penultimate and the ultimate fingers (i.e. the next-to-last and the last downstream fingers, respectively) are lifted off the tube at a rate which is different than the rate at which other fingers in the peristaltic mechanism lift off from the tube. This is done to compensate for the increase in pressure created by the downward movement of other fingers as they subsequently begin to pinch the tube when both the first and ultimate fingers are occluding the tube.

Stated differently, there are two (2) cooperative functions which take place simultaneously to minimize the discontinuity in fluid flow which occurs while the ultimate finger occludes the tube. Firstly, the time is shortened during which the ultimate finger occludes the tube. Secondly, while the ultimate finger and the first upstream finger are occluding the tube, the penultimate finger is lifting off the tube at a rate which compensates for the urging of other fingers against the tube. This is done to equalize fluid pressure in the pocket formed between the first upstream finger and the ultimate finger.

Additionally, the help reduce the pressure build up inside the tube when there are two (2) points of occlusion, the ultimate finger may be shortened with respect to the other fingers by approximately one hundredth of an inch (0.01") to reduce the total occlusion time of the ultimate finger. This correspondingly increases the occlusion time of the first finger. Obviously, the shortening of the last finger can be accomplished by either modification of its corresponding cam lobe or by actually reducing the length of the finger.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
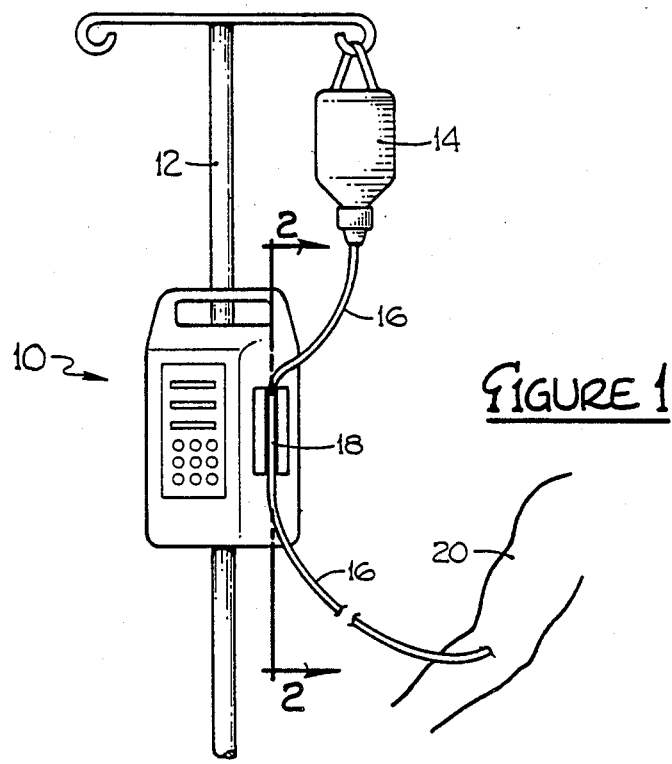
FIG. 1 is a front elevational view of a linear peristaltic pump incorporating the peristaltic mechanism shown in its working environment.

Referring initially to FIG. 1, a pump generally designated 10 is shown in its intended environment. The pump 10 is mounted on I.V. pole 12 in a manner well known in the art. An I.V. fluid source 14 is suspended from the I.V. pole 12 as shown in FIG. 1 and an I.V. tube 16 is connected in fluid communication with fluid source 14 and operatively connected with pump 10 in a manner as generally shown in FIG. 1. Tube section 18 of tube 16 is that portion of the tube operatively engaged by the pump 10. I.V. tube 16 is subsequently coupled to patient 20 for the infusion of fluid source 14 to patient 20.

Figure 2:
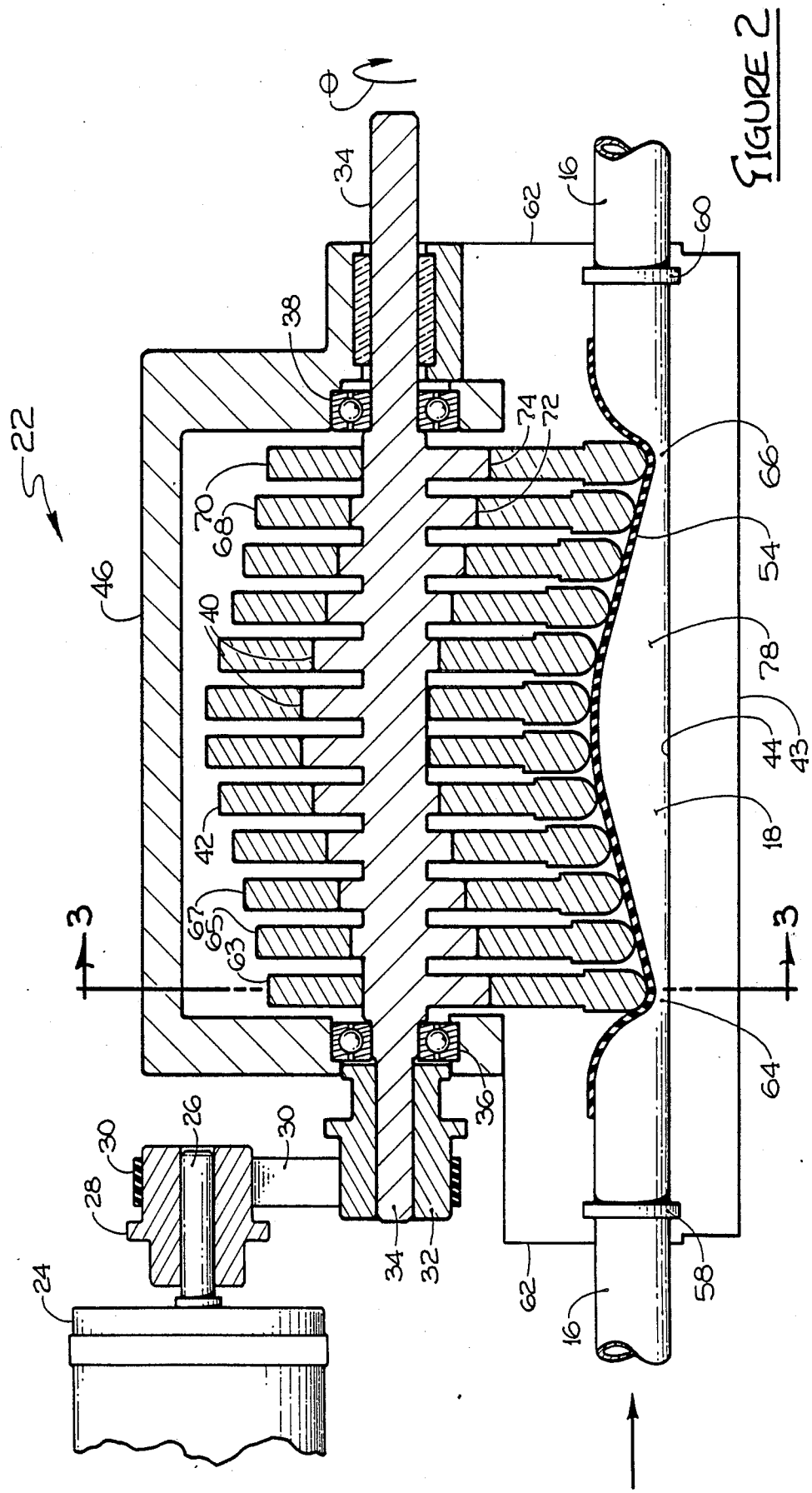
FIG. 2 is a cross-sectional view of the peristaltic mechanism showing the plurality of fingers as seen along line 2—2 in FIG. 1.

FIG. 2 is a cross-sectional view of the peristaltic mechanism, generally designated 22, which is shown here in isolation from pump 10 for purposes of clarity. As shown in FIG. 2, peristaltic mechanism 22 includes a motor 24 which is preferably a stepper motor but may be of any type well known in the relevant art. A drive shaft 26 is rotated by the motor 24 and is secured to an attachment 28 by any means well known in the art in a manner which permits the rotation of attachment 28 to move a drive pulley 30. Drive pulley 30 is connected in operative engagement with an attachment 32 that is in turn secured to camshaft 34 by any means well known in the art. Camshaft 34 is supported on peristaltic mechanism 22 by a bushing 36 and a bushing 38. As can be appreciated, bushings 36 and 38 are mounted within a casing 46. Integrally connected onto camshaft 34 at predetermined locations along the axis of the camshaft 34 is a series of cam lobes 40. As will be appreciated by those skilled in the pertinent art, cam lobes 40 are eccentrically mounted on camshaft 34 in a helical pattern along the axis of camshaft 34 and are engaged with finger 42 in a manner which creates a wave-like movement of fingers generally designated as 42 when camshaft 34 is rotated. Within the mechanism, the plurality of fingers 42 includes a penultimate finger 68 and an ultimate finger 70 which are operatively coupled to a corresponding penultimate cam lobe 72 and an ultimate cam lobe 74. In addition, for the embodiment described herein, there are also included a first finger 63, a second finger 65, and a third finger 67. The movement of the plurality of fingers 42, which includes both the penultimate finger 68 and ultimate finger 70, will best be appreciated by reference to FIG. 3. For the moment, however, all fingers and cam lobes wil be referred to generally as 42 and 40, respectively, for simplicity.

Figure 3:
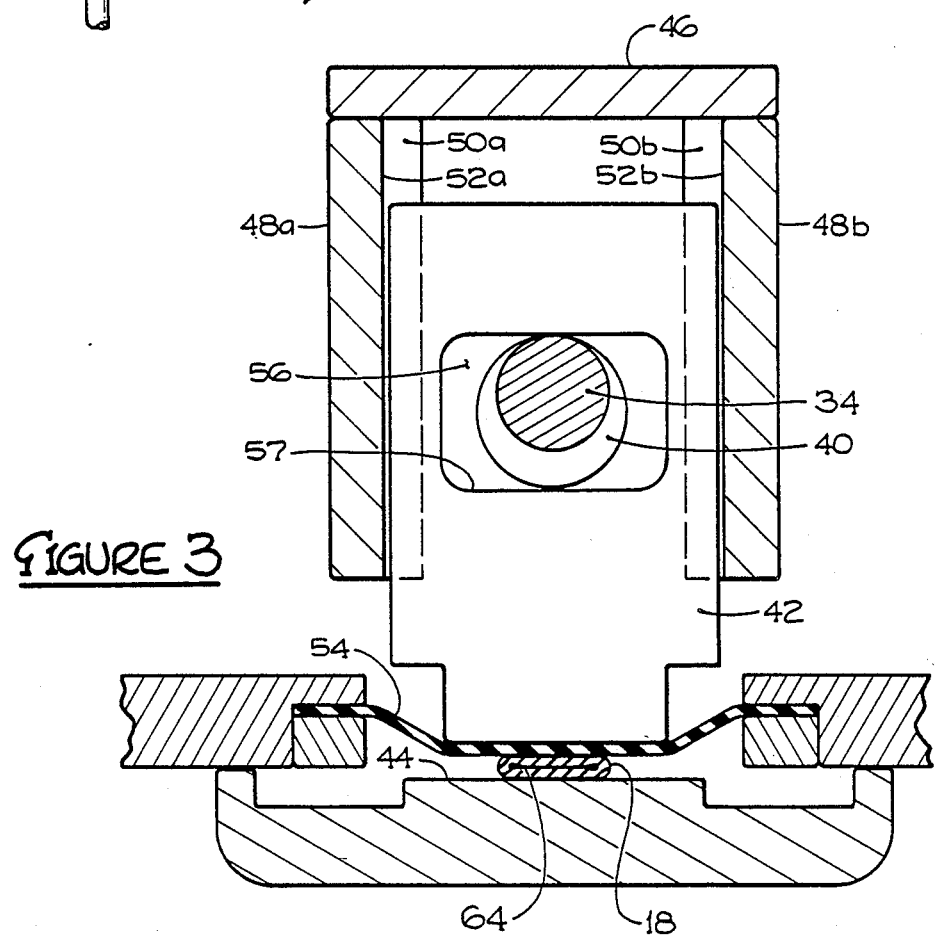
FIG. 3 is a cross-sectional view of a finger operatively connected to a cam lobe.

Referring to FIG. 3, it is seen that each of the individual fingers 42 are formed with an aperture 56 to receive the individual cam lobe 40 therein. Each finger 42 is mounted in casing 46 of the peristaltic mechanism 22 for movement in a direction substantially perpendicular to the longitudinal axis of camshaft 34. To accomplish this, the casing 46 has a side 48a and a side 48b which are formed with baffles 50a and 50b that create grooves 52a and 52b for maintaining the alignment of each respetive finger 42 relative to camshaft 34. The rotation of camshaft 34 rotates each eccentrically mounted cam lobe 40 so that it is urged against respective wall portions 57 of the aperture 56 to cause a reciprocal motion of finger 42 within the casing 46.

Referring again to FIG. 2, it can be appreciated by the skilled artisan that cam lobes 40 can be located along camshaft 34 in a helical manner. With cam lobes 40 so located, rotation of camshaft 34 about an axis substantially parallel to the tube causes fingers 42 to move sequentially in a direction substantially perpendicular to the axis of camshaft 34. This moves fingers 42 in a wave-like fashion to move I.V. solution 14 through tube 16 into patient 20.

The I.V. tube 16 can be placed in operation with peristaltic mechansim 22 by location of respective fitments 58 and 60 into the base 62 of peristaltic mechanism 22. As shown in FIG. 2, section 18 of I.V. tube 16 can be defined between fitment 58 and fitment 60. This particular section 18 may be made of the same material as I.V. tube 16. In the preferred embodiment, the section 18 comprises a very flexible and compressible material, such as a silicon rubber.

Once I.V. tube 16 and its associated pumping section 18 have been mounted on peristaltic mechanism 22, a door 43 can be closed to provide a platen 44 for supporting the tube 16 in substantially a linear orientation. The platen 44 provides resistance against the occluding movement of the fingers 42 as they sequentially urge on section 18 of the I.V. tube 16. A membrane 54 may be interposed between fingers 42 and tube section 18 to encase fingers 42 separately from pumping section 18 and to isolate I.V. tube 16 and section 18 from the peristaltic mechanism 22. Camshaft rotation angle $\theta$, and the helical orientation of appropriately shaped cam lobes 40 along camshaft 34, cooperatively designate the timing and amount of perpendicular movement of finger 42 along pumping section 18. Further, it will be appreciated that each complete revolution of camshaft 34 causes a complete cycle of sequential movement of fingers 42 to urge against section 18 to generate a peristaltic action of wavelike occlusion of the tube section 18.

OPERATION

In its operation, pump 10 is placed in operative engagment with an I.V. tube 16. This is done by positioning I.V. tube 16 against base 62 of peristaltic mechanism 22 as shown in FIG. 2. With tube 16 in its position, fitments 58 and 60 are operatively engaged with base 62. As discussed previously, the portion of I.V. tube 16 which is placed against membrane 54 and in operative engagement with pump 10 is preferably a flexible and compressible tube section 18.

Once I.V. tube 16 and its section 18 have been engaged with pump 10, the door 43 is closed. The closure of door 43 causes platen 44 to contact section 18 and enclose section 18 between platen 44 and membrane 54 for supporting the tube 16 in substantially a flat linear orientation.

Activation of stepper motor 24 rotates drive shaft 26 causing drive pulley 30 to rotate camshaft 34. The actual positioning of camshaft 34 is represented by camshaft rotation angle $\theta$. Revolution of camshaft 34 will cause the series of cam lobes 40 to reciprocate fingers 42 in a direction substantially perpendicular to the axis of section 18. Due to the helical configuration of cam lobes 40 on camshaft 34, fingers 42 are sequentially urged against section 18 to create a moving zone of occlusion along the length of section 18 during revolution of camshaft 34.

During operation of peristaltic mechanism 22, as shown in FIG. 2, rotation of camshaft 34 causes first finger 63 to occlude section 18 at point 64, and ultimate finger 70 to occlude at point 66. As can be seen, simultaneous occlusion at points 64 and 66 creates a pocket 78 within section 18 which is full of I.V. fluid 14. The pressure in pocket 78 increases further as the rotating camshaft 34 causes second and third fingers 65 and 67 to be urged against section 18. Ordinarily, if no pressure reduction mechanism is provided, when ultimate finger 70 subsequently lifts off pumping section 18, there will be a surge of fluid to patient 20. This surge is caused by the pressure which has been allowed to build up inside section 18. The present invention recognizes that the pressure in pocket 78 may be reduced by increasing the rate at which penultimate finger 68 and ultimate finger 70 are lifted off from the tube 16.

Figure 4A:
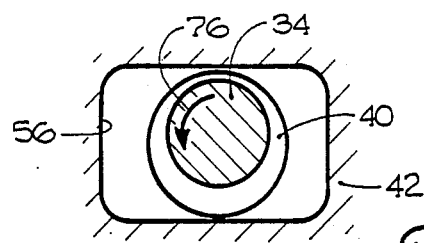
FIGS. 4A, 4B and 4C are cross-sectional views of cam lobes showing various configurations which correspondingly control the reciprocal movement of their associated fingers.
Figure 4B:
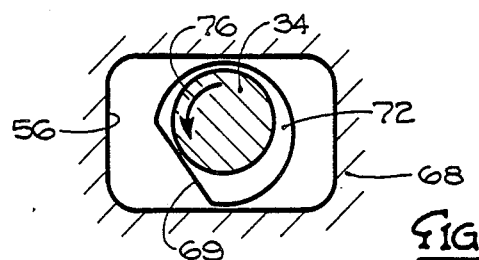
Figure 4C:
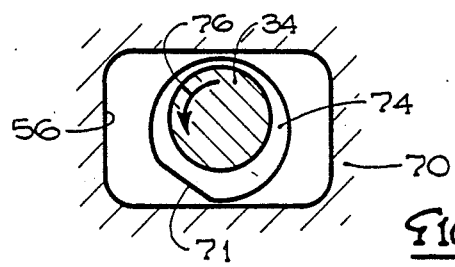

As can be seen in FIG. 4A, when camshaft 34 rotates in the direction of arrow 76, cam lobe 40 is correspondingly rotated within aperture 56. Rotation of cam lobe 40 reciprocates finger 42 between an up or open position and a down or closed position with respect to the center line of camshaft 34. The interaction between each finger 42 and helically positioned cam lobe 40 causes the fingers 42 to produce the reciprocal movement to sequentially urge the fingers 42 against the section 18 for moving fluid through the tube 16. Referring to FIG. 4B, the rate at which finger 68 is lifted off from section 18 can be increased by modifying the shape of penultimate cam lobe 72. Finger 68 can be lifted off of section 18 at a faster rate by providing a flat 69 which is integrally formed on the circumference of penultimate cam lobe 72. As shown in FIG. 4C, the rate of lift off of ultimate finger 70 can also be increased by provided a flat 71 which is integrally formed on the circumference of ultimate cam lobe 74. Flat 69 and flat 71 can be configured to control the rates of lift off of penultimate finger 68 and ultimate finger 70, respectively, from pumping section 18.

To aid further in linearizing the flow of fluid to patient 20, the amount of occlusion at point 66 may be reduced by shortening the stroke length of ultimate finger 70, or by further modifying flat 71 of ultimate cam lobe 74. Preferably, the amount of occlusion is modified by selectively forming the flat 71 of ultimate cam lobe 74 to shorten the reciprocal movement of the finger 70 in the direction of the tube 16. Alternatively, ultimate finger 70 may be shortened by approximately 1/100 of an inch as compared to the uniform length of the remaining plurality of the fingers 42. These modifications cause the occlusion time at point 66 to be reduced. As can be seen in FIG. 4C, flat 71 of ultimate cam lobe 74 is modified to displace the finger 70 such that its reciprocal movement toward the section 18 is shorter than the movement of the other fingers.

Figure 5:
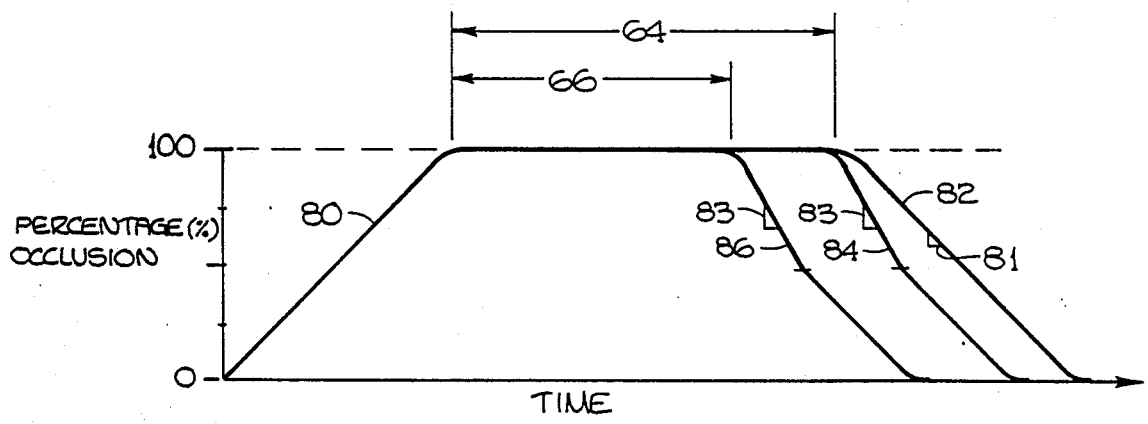
FIG. 5 is a graph showing the percent occlusion of the tube by the relative fingers with respect to time.

To further illustrate the interaction between fingers 42, penultimate finger 68 and ultimate finger 70, a graph is shown in FIG. 5 which illustrates the percent occlusion of each finger with respect to time, with zero (0) percent representing fully open, and one hundred (100) percent representing fully closed or fully occluded. Initially, fingers 42, penultimate finger 68 and ultimate finger 70 have identical rates of displacement against the section 18. This rate corresponds to a slope of line 80. As can be seen, the normal rate of lift of (i.e. the rate at which a finger 42 would normally lift away from section 18) can be seen by slope 81 for line 82. In order to increase the rate of lift off, the cam lobes 72 and 74 are modified to create a slope 83 for lines 84 and 86 which are steeper thus reflecting the increased rate of lift off of penultimate finger 68 and ultimate finger 70 from tube 16. Thus, penultimate finger 68 is lifted off section 18 more quickly, just as second and third fingers 65 and 67 are urged against the section 18, reducing pressure which would otherwise be allowed to build up in the pocket.

Still referring to FIG. 5, it can be seen also that the duration of the occlusion of points 64 and 66 are different. Specifically, occlusion point 66 has a relatively shorter occlusion time with respect to occlusion point 64 due to modifying the cam lobe 74 as previously discussed.

In sum, with the structure as described above, it is to be appreciated that penultimate finger 68 is lifted at a faster rate than fingers 42 in order to compensate for a possible build up in fluid pressure when both points 64 and 66 are simultaneously occluded. On the other hand, ultimate finger 70 is lifted at a faster rate than fingers 42 in order to decrease occlusion time at occlusion point 66 to thereby minimize the discontinuity in fluid flow through tube section 18.

While the particular linear peristaltic pump with a pressure relief mechanism as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. A linear peristaltic pump for creating a moving zone of occlusion along a resilient tube to pump fluid through the tube which comprises:
   a casing;
   a platen for supporting the tube in a substantially linear orientation;
   a camshaft mounted on said casing, said camshaft having a series of cam lobes each eccentrically mounted on said camshaft to establish a helical series therealong, the penultimate and ultimate cam lobes of said series each being formed with a flat;
   a plurality of fingers each operatively engaged with one of said respective cam lobes; and
   means for rotating said camshaft to produce a reciprocal movement of said fingers to sequentially urge said fingers against said tube and control the occlusion created by said fingers engaged with said penultimate and said ultimate cam lobes according to the location of said flat.

2. A linear peristaltic pump as recited in claim 1 wherein said menas for rotating said camshaft comprises a motor operatively coupled to said camshaft and fixedly mounted on said casing.

3. A linear peristaltic pump as recited in claim 2 wherein said casing has formed therein a plurality of internal grooves for receiving said plurality of fingers therein to constrain said fingers in said reciprocal movement.

4. A linear peristaltic pump as recited in claim 3 wherein said camshaft rotates about an axis substantially parallel to the tube.

5. A linear peristaltic pump as recited in claim 4 wherein said flats on said penultimate cam lobe and on said ultimate cam lobe are configured to lift said penultimate finger and said ultimate finger from the tube at a rate faster than the rate at which the other said fingers are lifted from the tube.

6. A linear peristaltic pump as recited in claim 5 wherein said flat of said ultimate cam lobe is formed to shorten the reciprocal movement of said finger in the direction of the tube.

7. A linear peristaltic pump as recited in claim 5 further comprising an ultimate finger operatively engaged with said ultimate cam lobe, said ultimate finger having a length shorter than each of said plurality of fingers.

8. A linear peristaltic pump for creating a moving zone of occlusion along a resilient tube for pumping fluid through the tube which comprises:
   a casing;
   a platen for supporting said tube in substantially a linear orientation;
   a plurality of fingers slidably mounted within said casing, said fingers serially aligned along the tube;
   means for reciprocally moving said fingers to sequentially urge said fingers against the tube; and
   means for lifting said penultimate finger and said ultimate finger from the tube at a rate faster than the rate at which the other of said fingers are lifted from the tube.

9. A linear peristaltic pump as recited in claim 8 wherein said means for reciprocally moving said fingers comprises:
   a camshaft rotatably mounted on said casing;
   a plurality of cam lobes eccentrically mounted on said camshaft to establish a helical series therealong for operable engagement with said plurality of fingers; and
   a motor fixedly mounted to said casing and coupled to said camshaft for rotating said camshaft.

10. A linear peristaltic pump as recited in claim 9 wherein said camshaft rotates about an axis substantially parallel to the tube.

11. A linear peristaltic pump as recited in claim 10 wherein said casing has formed therein a plurality of grooves for receiving said plurality of fingers therein to constrain said fingers for linear reciprocal movement.

12. A linear peristaltic pump as recited in claim 11 wherein said means for lifting said penultimate finger and said ultimate finger from said tube comprises a flat formed on said penultimate cam lobe and on said ultimate cam lobe.

13. A linear peristaltic pump as recited in claim 12 wherein said flat is integrally formed on the circumference of said cam lobe.

14. A linear peristaltic pump as recited in claim 13 wherein said flat on said ultimate cam lobe shortens the reciprocal movement of said finger in the direction of the tube.

15. A linear peristaltic pump as recited in claim 11 wherein said ultimate finger has a length shorter than that of the other plurality of fingers.

16. A method for linearizing fluid flow through a resilient tube in a linear peristaltic pump which pumps I.V. fluids with a series of fingers including a penultimate finger, an ultimate finger, and other fingers comprising the steps of:
   (A) Sequentially occluding a tube in wavelike fashion with said series of fingers to create a moving zone of occlusion along said tube;
   (B) Disengaging said penultimate finger from said tube at a rate faster than that of said other fingers;
   (C) Occluding the tube with said ultimate finger for a shorter period of time than that of said other fingers; and
   (C) Disengaging said ultimate finger from said tube at a rate faster than that of said other fingers.

* * * * *